United States Patent [19]

Sheingorn

[11] 4,429,961

[45] Feb. 7, 1984

[54] VISUAL FIELD TESTING DEVICE

[76] Inventor: Larry A. Sheingorn, 3139 Tennyson St., NW., Washington, D.C. 20015

[21] Appl. No.: 292,909

[22] Filed: Aug. 14, 1981

[51] Int. Cl.³ .............................................. A61B 3/02
[52] U.S. Cl. .................................... 351/226; 351/224
[58] Field of Search ............... 351/226, 224, 225, 246; 364/115

[56] References Cited

U.S. PATENT DOCUMENTS 3,288,546 11/1966 Gans ..................................... 351/226
4,260,227 4/1983 Munnerlyn et al. ................. 351/226

Primary Examiner—John K. Corbin
Assistant Examiner—Paul M. Dzierzynski
Attorney, Agent, or Firm—Charles R. Wolfe, Jr.

[57] ABSTRACT

An improved visual field testing device is disclosed. The device is a modification of an automatic Goldmann-type perimeter device which permits operation by the physician or technician.

4 Claims, 1 Drawing Figure

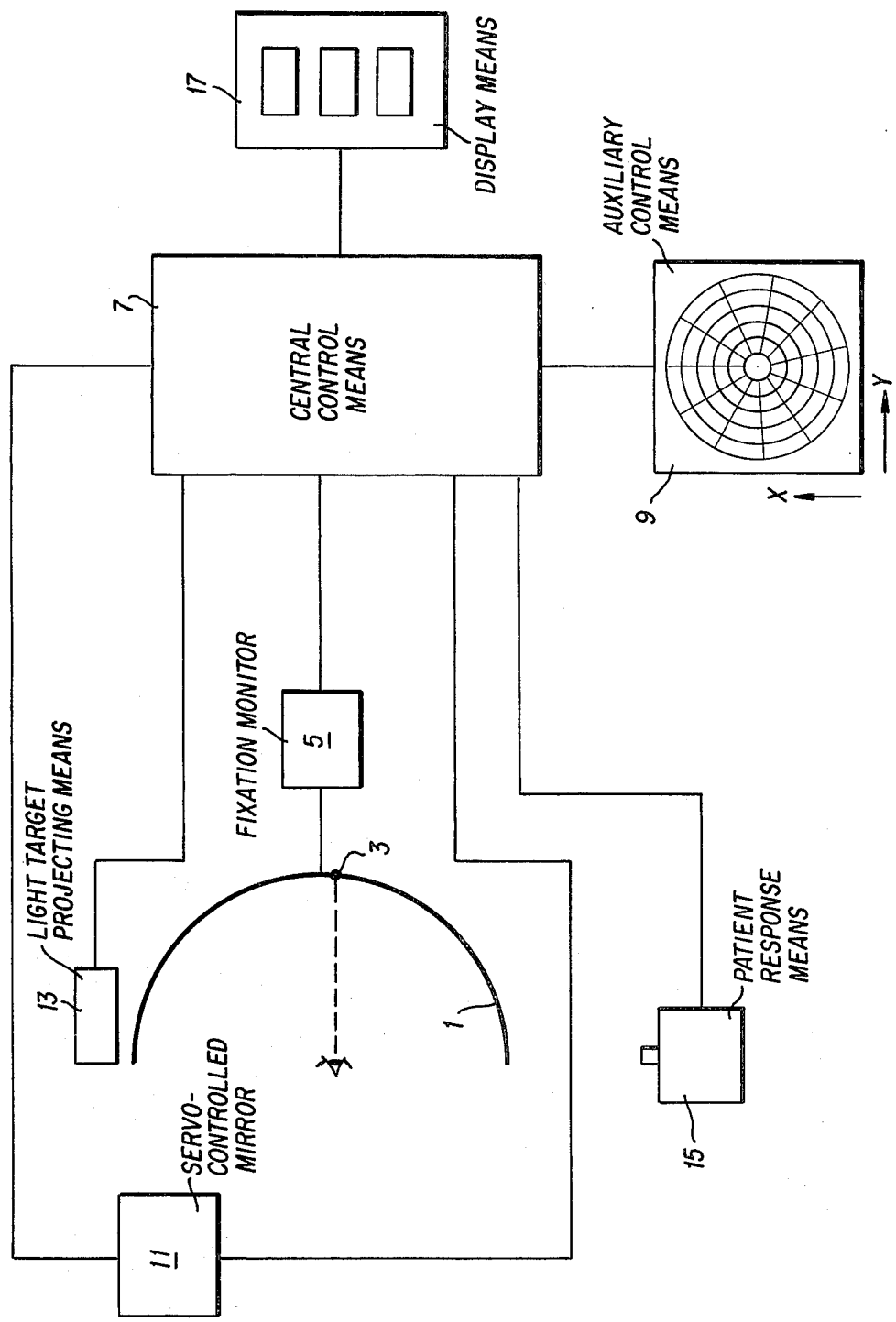

VISUAL FIELD TESTING DEVICE

BACKGROUND OF THE INVENTION

The invention is directed to an improved visual field testing device which enables a human operator to perform visual field tests faster and more reliably than heretofore possible with conventional human-operated devices.

Visual field tests are important tools of the ophthalmologist for detecting numerous diseases and defects of the eye, optic nerve and brain. In simplest form, a visual field test is conducted by sequentially displaying a series of individual light targets on a screen and noting those targets which can be seen by a patient whose eye is fixated on the center of the screen. The targets which the patient can see define the patient's visual field. Targets which the patient cannot see can be used to determine defects within the visual field. In kinetic perimetry tests, a light target is moved along a path from the outside of the patient's visual field until the patient responds to the stimulus. In static perimetry tests, the light targets are fixed points which do not move. Instead, the size and/or intensity may be increased until the patient responds to the stimulus.

Numerous devices have been designed to test visual fields. For example, U.S. Pat. No. 3,421,498 discloses a device comprised of a screen containing a plurality of apertures through which lights are sequentially shown. As the lights appear, the patient acknowledges vision by pressing a hand held button or switch. The response is automatically noted on a visual fiedl chart by a recorder. If the patient fails to see a light he does not respond and this is apparent on the chart.

Because this type of visual field tester utilizes a screen containing fixed lamps, it is not possible to conduct a highly detailed test of a section of the patient's visual field in the area between two adjacent lamps. In view of this shortcoming, many current visual field testing devices do not use screens containing fixed lamps but contain means for projecting an individual light target at any point on the screen.

Thus, in perhaps the best known visual field testing device, often referred to as a Goldmann perimeter, the operator positions a marker at a particular point on a visual field chart. The marker is connected to a light source by a lever arrangement which positions the source such that light is directed onto the screen corresponding to the point of location of the marker on the visual field chart. Because there are no fixed lamps, an infinite number of points within the visual field can be tested. However, it is often quite difficult to position the light source due to drifting and general instability of the lever connecting the light sources to the marker.

More recently, in U.S. Pat. No. 4,260,227, a device is disclosed which conducts visual field tests automatically. This device utilizes a stationary source of light which projects light onto a mirror which reflects it onto the screen. The mirror is rotatable along its axis and around the circumference of the perimeter bowl. By rotating the mirror around the circumference of the bowl and adjusting the angle of the mirror, the light can be directed to any point on the screen. The mirror is controlled by a servo-mechanism which is connected to a mini-computer which is programmed to sequentially adjust the position of the mirror through the servo-mechanism and to receive and record the responses of the patient.

However, because this device is fully automated, it cannot be used by an ophthalmologist to conduct an individualized visual field test. This is particularly important when the ophthalmologist is relying upon the test to aid him in planning a clinical or surgical $R_x$.

SUMMARY OF THE INVENTION

Accordingly, it is a primary object of the invention to provide a visual field testing device which possesses the reliability of the automated tester containing a servo-controlled mirror but permits a human operator to conduct the test.

Other objects and advantages of the invention will be apparent to those of skill in the art upon review of the detailed description contained herein.

These objects and advantages are provided by modifying the existing automated tester which utilizes a stationary source of light and servo-controlled mirror to direct the light onto the screen. In this device which is the subject of U.S. Pat. No. 4,260,227 (the entire disclosure of which is hereby incorporated by reference), a micro-processor, programmed to run a standard visual field test, issues mirror position signals to the servo-mechanism which rotates the mirror to direct the light onto the screen at the designated point.

For kinetic perimetry tests, the program is written such that a moving light target, referred to as a scan, will be displayed on the bowl, starting from a point outside the patient's visual field. The micro-processor is also connected to a hand held button which the patient presses to acknowledge vision. Upon receipt of the acknowledgement signal from the patient, the micro-processor records it at the appropriate point on the visual field chart for the patient and transmits a new series of mirror position signals to the servo-mechanism to begin a new scan. When the patient fails to respond to a light target in a scan, the micro-processor records the blind spot on the visual field chart and issues instructions for a new scan. The program for the micro-processor is written so that the instructions issued for a new scan will depend upon the results of the preceding scan.

The device can also be used to conduct static perimetry tests since it includes means for varying the size and intensity of the light target comprising a system of shutters having different sizes and filters.

The micro-processor is further connected to a fixation monitor which monitors the position of the patient's eye by known means.

The present invention modifies this automatic Goldmann-type device by including auxiliary control means which permits a human operator to select the points to be tested. When the auxiliary control means is engaged, the micro-processor does not run the automated testing program, but responds to signals generated at the auxiliary control means.

The auxiliary control means can be any apparatus which is capable of generating a signal which identifies a specific point on the visual field chart and transmits a mirror position signal to the servo-controlled mirror. The auxiliary control means also includes means to enable the operator to adjust other parameters of the test besides target position, such as the intensity and size of the light target.

BRIEF DESCRIPTION OF THE FIGURE OF DRAWING

The FIGURE of Drawing is a flow diagram of a visual field testing device in accordance with the invention.

DETAILED DESCRIPTION OF THE PREFERRED EMBODIMENT

Referring to the FIGURE of Drawing, a flow diagram of a device designed in accordance with the invention is shown. This device comprises a substantially hemispherically shaped screen 1 referred to as a perimeter bowl for displaying the light targets. The patient's head is placed in position within the bowl on a frame which minimizes head movement during the test.

The patient is positioned so that eye level is even with fixation light 3 in the center of the screen. During a test, the patient's eye must fixate on the fixation light to insure an accurate test. Fixation monitor 5 is provided to observe the fixation status of the patient at set intervals, e.g., every ¼ second, and to transmit a signal to the central control means 7 when the fixation status deviates beyond a predetermined point. The fixation monitor observes fixation status by known techniques, such as directing infra-red light at the eye which reflects off the concave surface of the cornea and back to the monitor where photocells record the intensity and location of light and compares these values to a fixation norm. If the observed values deviate from the norm for complete fixation beyond a predetermined amount, the monitor transmits this information to the central control means.

Central control means 7 is a micro-processor which is programmed to transmit and receive the signals necessary to control the various parts of the device and to receive and record the patient's responses and lack of responses.

The central control means is responsive to auxiliary control means 9 which is operated by the physician or technician. The auxiliary control means is most preferably an X-Y pad which is a commercially available device used to place information into a computer. The X-Y pad generates data that corresponds to the X and Y co-ordinates of any given point on the pad. The X-Y pad allows the operator to test any desired point on the visual field chart. A visual field chart is placed over the pad and by manually positioning a marker at any point on the chart, the exact position of the marker is transmitted to the central control means as X and Y co-ordinate data. The central control means interprets this data and transmits the appropriate mirror position data to the servo-controlled mirror 11.

The auxiliary control means also includes means for enabling the operator to adjust the size, intensity and/or color of the light target. Dials or keyboards are exemplary of such means. The dial or keyboard transmits a signal to the central control means which interprets it and transmits the appropriate control signal to a shutter assembly which controls the size, intensity and color of the light target.

Because the operator completes the visual field chart on the X-Y plotter of the auxiliary control means, there is no need for another visual field chart holder and stylus present in the device described in U.S. Pat. No. 4,260,277, although these items may be included to reproduce the test results. Thus, with the exception of the auxiliary control means, the device of the invention is identical to that described in the aforesaid patent. It includes means 13 for projecting a light target onto the servo-controlled mirror. This includes the shutter assembly for controlling the size, intensity and color of the light target. The device of the invention also includes response means 15 for the patient to acknowledge vision. These various means are described in detail in U.S. Pat. No. 4,260,277, and that description will not be reproduced herein.

However, it is understood that various modifications of the device can be made without departing from the spirit of the invention. For example, the device can be equipped with display means 17 which displays the target status, patient response status and fixation status for easy reference during a test.

While the invention has now been described in terms of various preferred embodiments, those of skill in the art will recognize that numerous additions, substitutions, omissions and modifications can be made. It is, therefore, intended that the scope of the invention be solely limited by the claims which follow.

I claim:

1. In an apparatus for automatically testing visual fields comprising:
    a bowl perimeter having an axis through its centerpoint;
    means for locating the head of a patient being test so that the axis of the patient's eye is approximately alinged with the axis of said bowl perimeter;
    a light source for projecting a target spot to a desired point of projection within said bowl perimeter;
    control means for moving the position of the target spot projection point relative to said bowl perimeter and for selectively projecting the target spot onto said bowl perimeter to determine points defining the visual field of the patient;
    the improvement comprising:
    auxiliary control means for generating data signals in response to a manually positioned marker placed on any point on a visual field chart and for transmitting said signals to said control means.

2. The apparatus as defined by claim 1, further comprising means associated with said auxiliary control means varying the size and intensity of the target spot produced by said light source.

3. The apparatus as defined by claim 1, wherein said auxiliary controls means is a pad that generates data signals corresponding to the x and y co-ordinates of any given point on the pad.

4. The apparatus as defined by claim 1, further comprising display means for displaying the target status, patient response status, and/or patient fixation status.

* * * * *

UNITED STATES PATENT AND TRADEMARK OFFICE
CERTIFICATE OF CORRECTION

PATENT NO. : 4,429,961

DATED : February 7, 1984

INVENTOR(S) : Larry A. Sheingorn

It is certified that error appears in the above-identified patent and that said Letters Patent is hereby corrected as shown below:

Column 4, line 34, "test" should read —tested—.

Signed and Sealed this

Fifteenth Day of May 1984

[SEAL]

Attest:

GERALD J. MOSSINGHOFF

Attesting Officer

Commissioner of Patents and Trademarks